United States Patent [19]

Ogle

[11] 4,182,326
[45] Jan. 8, 1980

[54] LARYNGOTRACHEAL SYRINGE

[75] Inventor: Robert W. Ogle, Newport Beach, Calif.

[73] Assignee: IMS Limited, South El Monte, Calif.

[21] Appl. No.: 828,248

[22] Filed: Aug. 26, 1977

[51] Int. Cl.$^2$ .............................................. A61M 5/00
[52] U.S. Cl. ................................................... 128/220
[58] Field of Search ............... 128/234, 235, 220, 221, 128/348, 351, 239, 215, 216

[56] References Cited

U.S. PATENT DOCUMENTS

| | | | |
|---|---|---|---|
| 3,086,525 | 4/1963 | Whitcomb | 128/348 X |
| 3,399,668 | 9/1968 | Lundgren | 128/348 X |
| 3,538,918 | 11/1970 | Engelsher et al. | 128/351 |
| 3,880,168 | 4/1975 | Berman | 128/351 |
| 3,885,561 | 5/1975 | Cami | 128/348 R |
| 3,941,131 | 3/1976 | Ogle | 128/220 X |
| 3,994,296 | 11/1976 | Cloyd | 128/220 |

*Primary Examiner*—John D. Yasko
*Attorney, Agent, or Firm*—Wills, Green & Mueth

[57] ABSTRACT

This patent describes a medicament injector for laryngotracheal anesthesia comprising a cylindrical vial having an open end and a closed end, a resilient plug inserted at least partially through said open end engaging the walls of said vail with a press fit, a cylindrical member having one closed end and a self-sustaining flexible curved and elongated cannula extending outwardly from said cylindrical member with a series of fluid discharge holes disposed radially thereabout over the portion of the path adjacent the free end, a thin, long fluid passage communicating with said cannula and extending inwardly into said cylindrical member with a sharpened inner end, cooperating threaded interlocking means on said cylindrical member and said plug, whereby upon interlocking the said plug with the said cylindrical member said vial is first held in an assembled but non-operating position and upon further interlocking of said plug with said cylindrical member said plug is pierced by said fluid passage and said passage communicates with said vial and said plug is locked securely to said cylindrical member to permit aspiration upon withdrawal of said vial, and to permit expulsion of the contents of said vial through said discharge holes in an essentially 360° array upon exertion of pressure on said vial.

1 Claim, 8 Drawing Figures

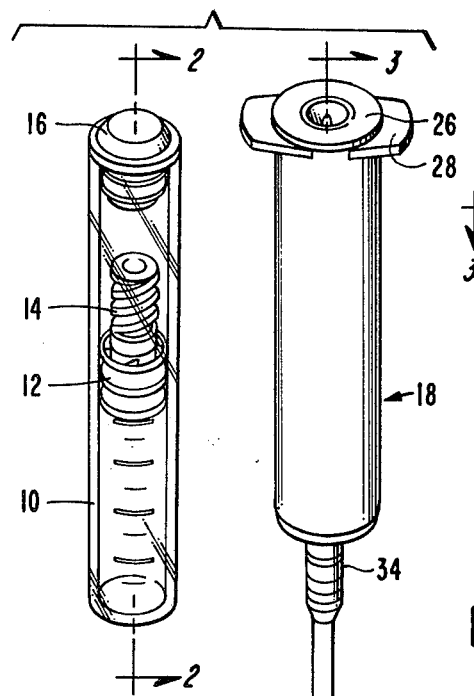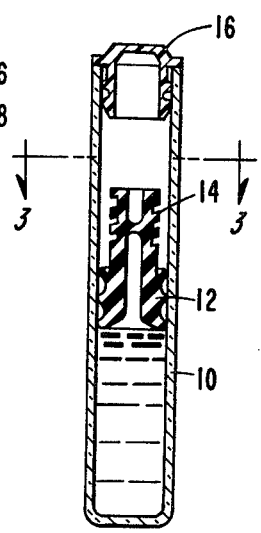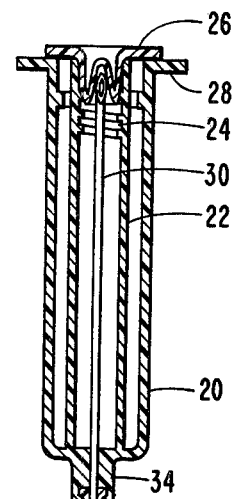
FIG.—1　　FIG.—2　　FIG.—3

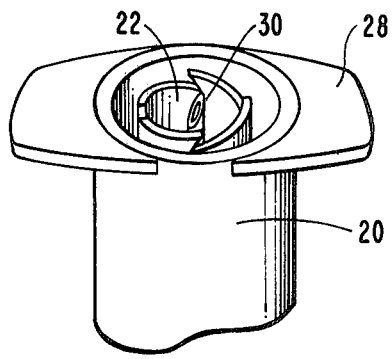
FIG.-4
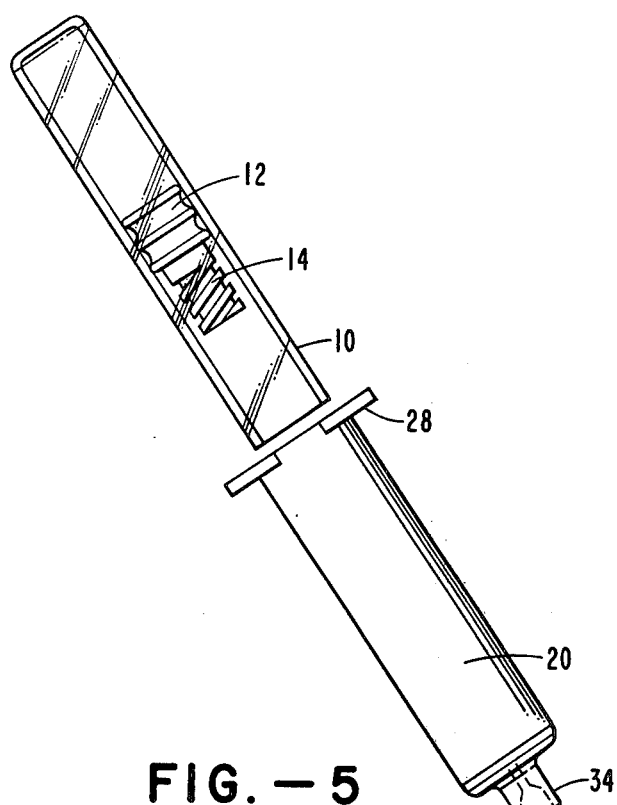
FIG.-5
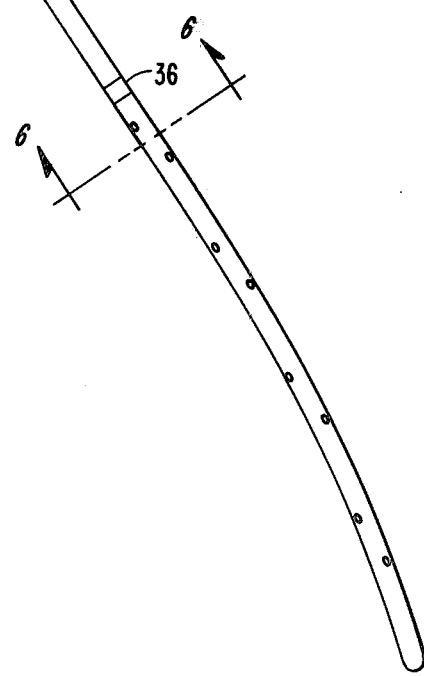
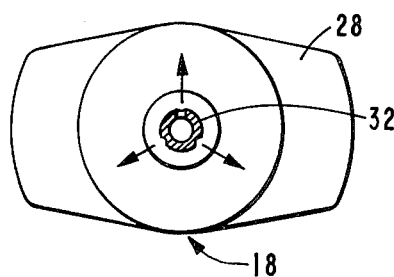
FIG.-6

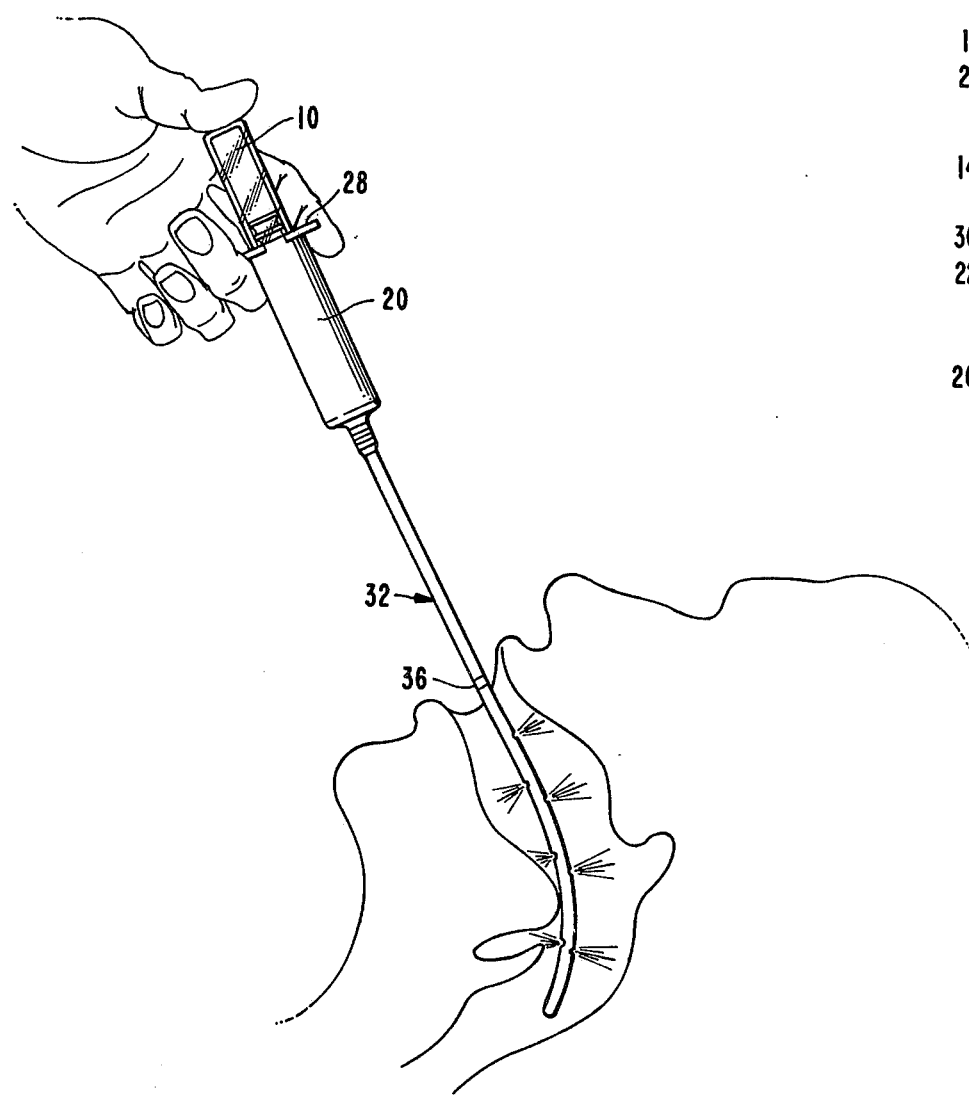
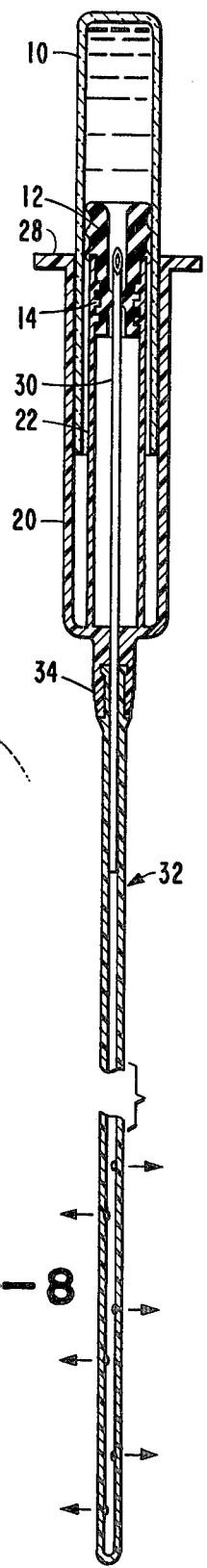
FIG.—7  FIG.—8

4,182,326

LARYNGOTRACHEAL SYRINGE

BACKGROUND OF THE INVENTION

A laryngotracheal syringe is shown in U.S. Pat. No. Des. 245,120 wherein the curved cannula is characterized by a series of in-line fluid discharge holes over the outer portion adjacent the free end. This device is intended for use in anesthetizing the tracheal area prior to various medical procedures. I have observed that the above-described device provides for discharge of the liquid anesthetic in only one direction or plane, and this discharge pattern provides inadequate assurance that the surrounding area of tissue will be adequately sprayed with the liquid anesthetic. I have solved this problem by the provision of a series of discharge openings along the outer half of the cannula wherein the openings are radially disposed thereabout at intervals of 120°. This configuration affords a discharge array which is essentially 360°. It is to be expected that this invention will be rapidly adopted by the medical profession.

SUMMARY OF THE INVENTION

Briefly, the present invention comprises a medicament injector for laryngotracheal anesthesia comprising a cylindrical vial having an open end and a closed end, a resilient plug inserted at least partially through said open end engaging the walls of said vial with a press fit, a cylindrical member having one closed end and a self-sustaining flexible curved and elongated cannula extending outwardly from said cylindrical member with a series of fluid discharge holes disposed radially thereabout over the portion of the path adjacent the free end, a thin long fluid passage communicating with said cannula and extending inwardly into said cylindrical member with a sharpened inner end, cooperating threaded interlocking means on said cylindrical member and said plug, whereby upon interlocking the said plug with the said cylindrical member said vial is first held in an assembled but non-operating position and upon further interlocking of said plug with said cylindrical member said plug is pierced by said fluid passage and said passage communicates with said vial and said plug is locked securely to said cylindrical member to permit aspiration upon withdrawal of said vial, and to permit expulsion of the contents of said vial through said discharge holes in an essentially 360° array upon exertion of pressure on said vial.

It is an object of the present invention to provide several improvements in the art of medicament injectors.

More specifically, it is an object of the present invention to provide a new means for laryngotracheal anesthesia.

Still another object of the present invention is to provide novel means for the spraying of a liquid anesthetic within the throat.

More particularly, it is an object of this invention to provide for more uniform administration of the liquid anesthetic in a laryngotracheal syringe.

These and other objects and advantages of this invention will be apparent from the more detailed description which follows, taken in conjunction with the accompanying drawings.

DESCRIPTION OF THE PREFERRED EMBODIMENTS

Turning to the drawings:

FIG. 1 is a side perspective view of the vial and syringe components of the invention in the form in which they are typically stored prior to use.

FIG. 2 is a sectional view of the vial of FIG. 1 taken along the line 2—2 in FIG. 1.

FIG. 3 is a sectional view of the syringe of FIG. 1 taken along the line 3—3 in FIG. 1.

FIG. 4 is a perspective view of the top or open end of the syringe.

FIG. 5 shows the relationship of the vial and syringe components as they are brought together for assembly.

FIG. 6 is a sectional view of the cannula taken along the line 6—6 in FIG. 5.

FIG. 7 shows the use of the assembled device in tracheal anethesia.

FIG. 8 is a sectional view of the device when assembled and in use, as in FIG. 7.

Considering the drawings in greater detail, the vial 10 is provided with a rubber stopper 12 having a threaded projection 14. The vial typically contains a liquid anesthetic such as lidocaine hydrochloride. A removable plastic dust cover 16 covers the open end of the vial during storage.

The syringe 18 has an outer barrel 20, an inner concentric cylindrical or thrust portion 22. The free end of thrust portion 22 has threads 24 which are adapted to be made up with the threaded projection 14 on stopper 12 to lock the vial to the syringe as shown in FIG. 8. The syringe 20 can also be provided with a removable plastic dust cover 26, and flanges 28 which facilitate the handling of the device, the aspiration thereof after assembly, and the holding of the device during administration of the anesthetic as shown in FIG. 7. A concentrically disposed cannula or needle 30 extends upwardly within the thrust portion 22 and preferably terminates within the walls thereof, as best shown in FIG. 4.

The curved cannula 32 is either permanently affixed to the boss 34 of syringe 20, as shown, or is removably attached to the syringe by a conventional Luer lock which is familiar to those skilled in the art. In any case, the cannula 32 is straight over approximately one-half its length and curved in a tracheal-like curve over the other or outer half. The outer or curved one-half is provided with a series of holes or discharge openings which are radially disposed at 120°, as best shown in FIG. 6. The end of cannula 32 may be closed as shown, or it may have an opening. In this way, when the liquid anethetic is discharged through the cannula, a "Christmas tree" array or spray in 360° pattern is emitted from the outer one-half of cannula 32.

In operation, the caps 16 and 26 are removed and the parts aligned as shown in FIG. 5. The vial 10 is then advanced into syringe 18, and the threads 14 and 24 are made up. The device can be aspirated at this point if so desired. The device is then ready for use as shown in FIG. 7.

The cannula 32 is preferably provided with insertion guide mark 36 which more or less coincides with the outer extremity of the patient's lips when the cannula has been advanced a proper distance for tracheal administration.

While this patent has particular application to laryngotracheal use, it is to be understood that the cannula can be modified, that is, it can be straight and shorter so as to be adapted for insertion into the nose, the use of such device otherwise being as indicated above.

Having fully described the invention, it is intended that it be limited only by the lawful scope of the appended claims.

What is claimed is:

1. A medicament injector for laryngotracheal anesthesia comprising a cylindrical vial having an open end and a closed end, a resilient plug inserted at least partially through said open end engaging the walls of said vial with a press fit, a cylindrical member having one closed end and surrounded by an outside barrel coextensive in length with said cylindrical member, a self-sustaining flexible and elongated cannula secured to and extending outwardly from said cylindrical member with a series of uniformly spaced fluid discharge holes disposed radially thereabout at an angle of about 120° over the one-half of the cannula adjacent the free end and an inserting guide mark provided on the exterior of said cannula at a location essentially halfway between the two ends of said cannula, said cannula being curved over about one-half of its length adjacent said free end and otherwise straight, said free end being rounded and closed, a thin long fluid passage communicating with said cannula and extending inwardly into said cylindrical member with a sharpened inner end, cooperating threaded interlocking means on said cylindrical member and said plug, whereby upon interlocking said plug with said cylindrical member said vial is first held in an assembled but non-operating position and upon further interlocking of said plug with said cylindrical member said plug is pierced by said elongated fluid passage and said passage communicates with said vial and said plug is locked securely to said cylindrical member to permit aspiration upon withdrawal of said vial, and to permit expulsion of the contents of said vial through said discharge holes in an essentially 360° array upon exertion of pressure on said vial.

* * * * *